United States Patent [19]

Montgomery

[11] Patent Number: 5,098,696

[45] Date of Patent: Mar. 24, 1992

[54] METHOD OF MAKING ARTIFICIAL FINGERNAILS

[75] Inventor: Robert E. Montgomery, Los Angeles, Calif.

[73] Assignee: REM Systems, Inc., Los Angeles, Calif.

[21] Appl. No.: 389,054

[22] Filed: Aug. 2, 1989

Related U.S. Application Data

[62] Division of Ser. No. 254,733, Oct. 7, 1988, Pat. No. 4,871,534.

[51] Int. Cl.$^5$ ............................................. A61K 7/043
[52] U.S. Cl. .................................... 424/61; 424/78.03; 525/259; 525/303; 512/113; 512/105; 427/2
[58] Field of Search .................. 424/61, 81; 525/259, 525/303, 939, 255, 100, 301

[56] References Cited

U.S. PATENT DOCUMENTS

| | | | |
|---|---|---|---|
| 4,104,333 | 8/1978 | Lee, Jr. | 424/61 |
| 4,229,431 | 10/1980 | Lee, Jr. | 424/61 |
| 4,260,701 | 4/1981 | Lee, Jr. | 424/61 |
| 4,289,752 | 9/1981 | Mahieu | 424/61 |
| 4,626,428 | 12/1986 | Weisberg | 424/61 |
| 4,669,491 | 6/1987 | Weisberg | 424/70 |
| 4,762,703 | 8/1988 | Abrutyn | 424/61 |
| 4,871,534 | 10/1989 | Montgomery | 424/61 |

*Primary Examiner*—Thurman K. Page
*Assistant Examiner*—D. Colucci
*Attorney, Agent, or Firm*—Blakely, Sokoloff Taylor, Zafman

[57] ABSTRACT

The present invention describes compositions that are useful for making artificial fingernails, in particular such compositions that are odorless, non-toxic, self-curing, and demonstrate good working properties as described above.

Compositions in accordance with this invention consist of two parts:

(a) an odorless, non-toxic liquid binder comprising one or more methacrylate monomer(s) of the following formula:

$$R-O-CH_2CH_2-O-CH_2C-H_2-O-CO-C(CH_3)=CH_2$$

where R is $CH_3(CH_2)_n$ and n = 0–3 together with one or more di-, tri-, or multi-functional methacrylates, and a teriary-amine type accelerator; and (b) a polymeric powder containing a finely divided methacrylate polymer or copolymer, and a peroxide polymerization initiator.

Upon mixing the above two components and subsequently shaping the resulting dough-like mass on a human fingernail, a hard, fused polymer is obtained in the shape of an artificial fingernail in from about 60 seconds to about 180 seconds at ambient temperatures.

15 Claims, No Drawings

METHOD OF MAKING ARTIFICIAL FINGERNAILS

This is a division of application Ser. No. 254,733, Oct. 7, 1988, now U.S. Pat. No. 4,871,534.

FIELD OF THE INVENTION

This invention relates to compositions that are useful for forming artificial fingernails and protective coatings on human fingernails. In particular, the present invention comprises odorless, self-curing compositions that can be applied over human fingernails to protect, adorn, extend, and/or decorate them.

BACKGROUND OF THE INVENTION

The prior art describes a variety of useful, self-curing compositions that can be applied to human fingernails to form an artificial nail. In general, these compositions are two-part systems which consist of a liquid portion (herein referred to as a binder) and a powder portion (herein referred to as a polymeric powder). The liquid binder comprises the following ingredients:
  (a) a monomeric acrylate or methacrylate ester such as ethyl methacrylate or tetrahydrofurfuryl methacrylate, and
  (b) a di-, tri-, or multi-functional acrylate or methacrylate ester such as ethylene glycol dimethacrylate or 1,4-butanediol dimethacrylate, and
  (c) a tertiary amine accelerator such as N,N-dimethyl-para-toluidine.

Optionally, the liquid binders may be seen to obtain polymerization inhibitors, such as BHT, dyes, and light stabilizers.

The polymeric powder portion of the prior art compositions generally comprise the following ingredients:
  (a) a polymeric methacrylate such as poly(ethyl methacrylate) or copolymeric methacrylate such as a 70/30 molar ratio poly(ethyl-co-methyl methacrylate), and
  (b) a peroxide polymerization initiator such as benzoyl peroxide.

Optionally, these polymeric powder portions may contain pigments, such as titanium dioxide, secondary polymers, such as poly(vinyl acetate), and flow modifiers such as fumed silica.

The practice of forming an artificial fingernail in situ (i.e., on a human fingernail) is a very exacting art. An artist's-type brush is first dipped in a reservoir containing the liquid binder portion, then transferred to a reservoir containing the polymeric powder portion. The wetted brush is allowed to contact the polymeric powder in such a way as to absorb sufficient powder to form a dough-like mass at the end of the brush. This dough is transferred to the surface of the human fingernail and subsequently shaped with the brush to form the desired coating and/or artificial fingernail extension. As is known in the art, when an extension is desired, a substrate form is used, and the dough is applied along the nail and form to provide an integrated extension. In the process of mixing the liquid binder with the polymeric powder, a free-radical polymerization process is initiated by the combination of the peroxide (in the polymeric powder portion) with the tertiary amine (in the liquid binder portion). The proper balancing of initiator and accelerator, and liquid binder and polymeric powder, allows sufficient working time to shape the desired artificial fingernail before the dough like mass polymerizes to a hard, fused plastic. The curing time is generally from about 60 seconds to about 240 seconds from the time of initial mixing of liquid and powder.

A critical parameter in the formulation of artificial fingernail compositions is the consistency of the above described dough-like mass that is formed on the artist's brush. A consistency that can be easily moved and shaped with the brush, yet does not slump or sag is considered ideal. The key to achieving such working properties lies in the correct matching of liquid binder components with polymeric powder components. The liquid binder must display sufficient solvency properties in order to dissolve, or at least partially dissolve the polymeric powder. The converse must also be true; that the polymeric powder must be selected such that it is soluble or at least partially soluble in the liquid binder to achieve the desired consistency of the dough-like mass.

Variables that can be adjusted in the polymeric powder portion include choice of polymer or copolymer used (molecular weight of polymer, ratio of chain elements in a copolymer, etc.), particle size distribution of the polymer powder, and inclusion of flow modifiers in the polymeric powder portion. The liquid binder portion can be varied as to its solvency properties for a given polymeric powder, and this, in turn, is based on the particular choice of monomeric acrylates and/or methacrylates for the liquid binder.

There has been much concern recently in the artificial fingernail industry over the potential toxicity from inhaling the monomeric acrylates and/or methacrylates utilized in the liquid binder portion of these compositions. Accumulation of monomer vapors in the workplace is certainly cause for concern, and is obvious to any nail technician due to the strong odors given off by most of the liquid binders that are available commercially.

Prior art compositions are based on liquid binders that contain monomeric acrylates and/or methacrylates with easily detectable odors. In addition, the inclusion of acrylate monomers (in addition to di-, tri-, and multifunctional acrylates) is considered a toxicological hazard in compositions intended for human contact. Thus, it would be advantageous to formulate a liquid binder with very little or no detectable odor that retained the correct working properties for making artificial fingernails.

Relevant prior art compositions are described in U.S. Pat. Nos. 3,539,533, 4,104,333, 4,058,442, 4,229,431, and 4,260,701. The acrylate and/or methacrylate monomers that are the subject of these inventions have distinctly detectable odors or have toxicity profiles that prelude their use for cosmetic applications. Particularly relevant is U.S. Pat. No. 4,260,701, which describes compositions useful for making artificial fingernails which are comprised of a major portion of methoxyethyl methacrylate. While methoxyethyl methacrylate possesses a mild, characteristic odor, recent studies have shown that there is a risk that the ethylene glycol monoether methacrylates of this kind may cause of possible birth defects. Similarly, ethoxyethyl methacrylate and butoxyethyl methacrylate fall into this same class of compounds and are toxicologically unsuitable for compositions intended for human contact.

BRIEF SUMMARY OF THE INVENTION

The present invention describes compositions that are useful for making artificial fingernails, in particular such compositions that are odorless, non-toxic, self-curing, and demonstrate good working properties as described above.

Compositions in accordance with this invention consist of two parts:

(a) an odorless, non-toxic liquid binder comprising one or more methacrylate monomer(s) of the following formula:

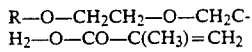
R—O—CH$_2$CH$_2$—O—CH$_2$C-
H$_2$—O—CO—C(CH$_3$)=CH$_2$ where R is CH$_3$(CH$_2$)$_n$ and n=0−3
together with one or more di-, tri-, or multi-functional methacrylates, and a teriary-amine type accelerator; and (b) a polymeric powder containing a finely divided methacrylate polymer or copolymer, and a peroxide polymerization initiator.

Upon mixing the above two components and subsequently shaping the resulting dough-like mass on a human fingernail, a hard, fused polymer is obtained in the shape of an artificial fingernail in from about 60 seconds to about 180 seconds at ambient temperatures.

DETAILED DESCRIPTION OF THE INVENTION

This invention comprises substantially odorless, non-toxic compositions that are useful for making artificial fingernails and/or decorative coatings on human nails. These compositions comprise a liquid binder and a polymeric powder, which, upon being admixed at the time of use, polymerize to a hard, fused polymer in the shape of an artificial fingernail and/or decorative coating in from about 60 seconds to about 180 seconds at ambient temperatures. The liquid binder portion is comprised of the following ingredients, based upon the total weight of liquid binder:

(a) from about 10 percent to about 95 percent of a methacrylate monomer of the formula

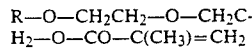
R—O—CH$_2$CH$_2$—O—CH$_2$C-
H$_2$—O—CO—C(CH$_3$)=CH$_2$ where R is CH$_3$(CH$_2$)$_n$ and n=0−3

(b) from about 4.9 percent to about 89.9 percent of a di-, tri-, or multi-functional methacrylate crosslinker, and (c) from about 0.1 percent to about 5.0 percent of a tertiaryamine type free-radical polymerization accelerator.

In addition to the above components, the liquid binder may optionally contain a polymerization inhibitor such as butylated hydroxytoluene or the methyl ether of hydroquinone (MEHQ) to prevent premature reaction of the methacrylate monomers and to assure adequate shelf life. Also, light stabilizers, such as 2-hydroxy-4-methoxy-benzophenone can be included in the liquid binder portion to prevent light-activated polymerization and to give the resulting polymer fingernail that is formed resistance to yellowing from ultraviolet light. Finally, auxilliary components such as dyes and secondary methacrylate monomers may be included so as to modify color and post-cure properties, respectively.

The polymeric powder portion is comprised of the following ingredients, based upon the dry weight of polymeric powder:

(a) from about 95 percent to about 99.5 percent of a finely divided polymer selected from poly(ethyl methacrylate), poly(ethyl-co-butyl methacrylate), poly(ethyl-co-methyl methacrylate), poly(methyl-co-butyl methacrylate) and mixtures thereof.

(b) from about 0.5 percent to about 3.0 percent of a peroxide free-radical polymerization initiator.

In addition to the above ingredients, the polymeric powder portion of the inventive composition may optionally contain pigments, such as titanium dioxide, secondary polymers, such as finely divided poly(vinyl acetate), and/or flow modifiers, such as fumed silica.

An essential ingredient in the present inventive composition is one or more of a class of odorless methacrylate monomers that makes up a majority, preferably from about 30 percent to about 90 percent by weight, of the total liquid binder. These methacrylate monomers are unique in their combination of high solvency, low volatility, low toxicity, and lack of odor, and are described in general by the formula:

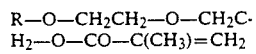
R—O—CH$_2$CH$_2$—O—CH$_2$C-
H$_2$—O—CO—C(CH$_3$)=CH$_2$ where R is CH$_3$(CH$_2$)$_n$ and n=0−3
More specifically, these odorless methacrylate monomers are derivatives of diethylene glycol monoethers, differing only in the substituent R group, which ranges preferably from one to four carbon atoms in length. The relevant compounds include methoxyethoxyethyl methacrylate, ethoxyethoxyethyl methacrylate, propoxyethoxyethyl methacrylate, isopropoxyethoxyethyl methacrylate, butoxyethoxyethyl methacrylate, isobutoxyethoxyethyl methacrylate, and tertiary-butoxyethoxyethyl methacrylate. These methacrylate monomers are unique in their lack of odor, low toxicity and low volatility, while still retaining the solvent properties necessary to obtain the correct working consistency for artificial fingernail use.

As mentioned above, secondary methacrylate monomers may be included in the liquid binder portion so as to modify the mechanical properties of the cured polymer fingernail/coating. Only those methacrylate monomers having little or no odor are included in the liquid binder of the present invention, generally in an amount from about 5 percent to about 65 percent by weight of liquid binder. The preferred secondary methacrylate monomers are hydroxyethyl methacrylate, hydroxypropyl methacrylate, hydroxybutyl methacrylate, tetrahydrofurfuryl methacrylate, and mixtures thereof. Tetrahydrofurfuryl methacrylate possesses a mild, distinct odor, therefore limiting it's concentration in the liquid binder to an amount not greater than about 20 percent by weight of liquid binder. The most preferred secondary methacrylate monomer is hydroxyethyl methacrylate in an amount from about 10 percent to about 30 percent by weight of liquid binder.

One or more di-, tri-, and/or multi-functional methacrylates (herein referred to as polyfunctional methacrylates) are included in the liquid binder portion to serve as crosslinkers. These polyfunctional methacrylates serve to increase the mechanical strength of the cured polymer fingernail/coating, improving such properties as stiffness, tensile strength, abrasion resistance, and chemical resistance. The shorter chain dimethacrylates and the tri- or higher methacrylates tend to give more brittle cured polymer properties, while the longer chain dimethacrylates result in cured polymers that are tough, yet fairly flexible, and are therefore preferred. To obtain the desired cured polymer properties, careful selection of and formulation with these polyfunctional methacrylates is necessary as is known in the art. Although any polyfunctional methacrylate or combination of polyfunctional methacrylates is contemplated in the present invention, the following polyfunctional methacrylates have been found to be particularly useful: ethylene glycol dimethacrylate, diethylene glycol dimethacrylate, triethylene glycol dimethacrylate, tetraethylene glycol dimethacrylate, polyethylene glycol dimethacrylate, dipropylene glycol dimethacrylate, tripropylene glycol dimethacrylate, 1,4-butanediol dimethacrylate, 1,3-butanediol dimethacrylate, 1,6-hexanediol dimethacrylate, 1,5-hexanediol dimethacrylate, neopentyl glycol dimethacrylate, 1,12-dodecanediol dimethacrylate, 2,2-bis[4'-(3''-methacryloyl -2''-hydroxypropoxy)-phenyl]propane (bis-GMA), 2,2-bis(4'-methacryloyl phenyl)propane (bis-phenol A dimethacrylate), ethoxylated bis-phenol A dimethacrylate, tetraethoxylated bis-phenol A dimethacrylate, dimethacrylate-terminated aliphatic and aromatic urethanes, trimethylolpropane trimethacrylate, pentaerythritol tetramethacrylate, and mixtures thereof. Methacrylate terminated and/or functional polymers are also contemplated, such as the hydroxyethyl methacrylate adducts of styrene/-maleic anhydride copolymers and methyl vinyl ether/-maleic anhydride copolymers.

The essential methacrylate monomers of this invention have the following general formula:

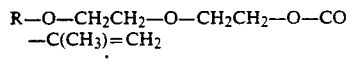

where $R = CH_3(CH_2)_n$ and $n = 0-3$
and are characterized by their low volatility, low toxicity, good solvency, and high reactivity in free-radical type polymerization reactions. In addition, these methacrylate monomers are virtually or completely free of any discernable odor, and yield cured polymers of moderately high tensile strength and outstanding flexibility. The preferred methacrylate monomers of this group are methoxyethoxyethyl methacrylate and ethoxyethoxyethyl methacrylate. In general, the liquid binder of this invention should contain one or more of the essential methacrylate monomers described above, a polyfunctional methacrylate to provide crosslinking, mechanical strength and durability, and a tertiary-amine as an accelerator for the free-radical polymerization process.

The tertiary amine accelerators are generally known in the art, and are preferably aromatic teriary amines such as N,N-dimethyl-p-toluidine, N,N-dihydroxyethyl-p-toluidine, N,N-dimethyl aniline, and/or 4-(dimethylamino)phenethyl alcohol (U.S. Pat. No. 4,284,551). The accelerator is usually employed at a concentration of from about 0.1 percent to about 5.0 percent by weight of liquid binder. The preferred tertiary amine accelerators are N,N-dimethyl-p-toluidine and N,N-dihydroxyethyl-p-toluidine.

The liquid binder may optionally contain auxilliary components such as dyes, polymerization inhibitors such as BHT and/or MEHQ and ultraviolet light absorbers such as 2-hydroxy-4-methoxy-benzophenone (Uvinul M-40, BASF/Wyandotte).

The polymeric powder portion that is combined with the liquid binder at the time of use is preferably a polymer or copolymer of ethyl or methyl methacrylate. Finely divided poly(ethyl methacrylate), poly(ethyl-co-methyl methacrylate), poly(ethyl-co-butyl methacrylate), and poly(methyl-co-butyl methacrylate) have been found most suitable for the practice of this invention. These finely divided polymers or copolymers are generally included in the powder portion at from about 80 percent to about 99.5 percent by weight of polymeric powder.

A peroxide initiator is also included in the polymeric powder in order to initiate the free-radical polymerization of the liquid binder/polymeric powder dough or mass upon mixing. The preferred peroxide initiators are benzoyl peroxide and lauroyl peroxide, which are present in a finely divided form, and well dispersed or blended in the polymeric powder portion. These initiators are present at from about 0.5 percent to about 3.0 percent by weight of polymeric powder. The most preferred peroxide initiator is benzoyl peroxide.

The polymeric powder portion may optionally contain flow modifiers such as fumed silica and/or secondary finely divided polymers such as poly(vinyl acetate). Flow modifiers serve to adjust or modify the working properties of the admixed liquid binder and polymeric powder for easier manipulation. In addition, the polymeric powder may contain pigments such as titanium dioxide, and/or fillers such as hydrated alumina, finely divided glass powder, or silicon dioxide.

As mentioned previously, the present invention consists of a liquid binder portion and a polymeric powder portion. These two portions are combined at the time of use to shape or form an artificial fingernail/coating. The preferred ratio of liquid portion to powder portion is from about 1 to 3 to about 2 to 1 by weight, and most preferably from about 1 to 3 to about 1 to 1 by weight. The liquid portion is packaged separately from the powder portion, preferably in light-resistant containers. The powder may be packaged in any moderately air and water resistant container.

The compositions of this invention are formulated such that there is sufficient working time for shaping the artificial fingernail/coating after mixing the liquid binder with the polymeric powder. The most practical polymerization or setting time for these compositions is from about 60 seconds to about 180 seconds, measured from the time of initial mixing of liquid binder and polymer powder. Preferably, the setting time is from about 90 seconds to about 150 seconds from the time of mixing.

EXAMPLES

The following examples are of compositions that have found particular utility in the artificial fingernail art.

| Example 1 | |
|---|---|
| Liquid Binder | |
| Methoxyethoxyethyl methacrylate | 70.0% |
| Ethylene glycol dimethacrylate | 18.5 |
| Hydroxyethyl methacrylate | 10.0 |
| MEHQ | [100.0 ppm] |
| BHT | [800.0 ppm] |
| Dimethyl-p-toluidine | 1.4 |
| | 100.0 percent |
| Polymeric Powder | |
| Poly(ethyl methacrylate) | 98.4% |

-continued

| Example I | |
|---|---|
| Benzoyl peroxide | 1.6 |
| | 100.0 percent |

The above components, when combined in a ratio of approximately one part liquid binder to about two parts polymeric powder, result in a suitably workable slurry or dough for shaping an artificial fingernail. The shaped mass will then be observed to cure to a hard fused polymer fingernail in approximately 120 seconds from the beginning of mixing.

EXAMPLE 1A

Most importantly, the liquid binder portion of Example I possesses a barely detectable odor, which was not observed to accumulate over long periods of time in containers open to the room atmosphere. The lack of accumulated vapors of the liquid binders of the present invention is best seen in a comparison between the vapor pressures of the above formulation and a typical commercially avialable binder. The commercially available liquid binder contained the following:

| Ethyl methacrylate | 91.6 |
|---|---|
| Ethylene glycol dimethacrylate | 7.0 |
| MEHQ | [30.0 ppm] |
| Dimethyl-p-toluidine | 1.4 |
| | 100.0 percent |

The vapor pressures of the Example I binder and the commercially available binder discussed above are as follows:

| Liquid Binder | Vapor Pressure |
|---|---|
| Example I | 0.02 |
| Commercial product | 7.65 |

The dramatically lower vapor pressure of the liquid binder of Example I is a general indication of its lower volatility, and thus, the lower tendency towards vapor accumulation.

| Example II | |
|---|---|
| Methoxyethoxyethyl methacrylate | 40.0 |
| Ethylene glycol dimethacrylate | 27.9 |
| Hydroxyethyl methacrylate | 31.0 |
| MEHQ | [100. ppm] |
| BHT | 0.1 |
| Dihydroxyethyl-p-toluidine | 1.0 |
| | 100.0 percent |

The above liquid binder, when combined with the polymeric powder portion of Example I, forms a hard, fused polymer in approximately 140 seconds from the beginning of mixing.

| Example III | |
|---|---|
| Ethoxyethoxyethyl methacrylate | 76.0 |
| Trimethylolpropane trimethacrylate | 7.9 |
| Hydroxyethyl methacrylate | 6.5 |
| 1,12-Dodecanediol dimethacrylate | 8.0 |
| MEHQ | [200 ppm] |
| BHT | [800 ppm] |
| Dimethyl-p-toluidine | 1.5 |

-continued

| Example III | |
|---|---|
| | 100.0 percent |

The above liquid binder is combined with a polymeric powder portion consisting of the following:

| Poly(ethyl-co-methyl methacrylate) [90:10] | 98.7 |
|---|---|
| Benzoyl peroxide | 1.2 |
| Titanium dioxide | 0.1 |
| | 100.0 percent |

When the above portions are combined in a ratio of approximately one part liquid to 1.8 parts polymeric powder, a white, hard, fused polymer results. This type of pigmented polymer finds utility in fashioning naturally colored artificial fingernails.

| Example IV | |
|---|---|
| Methoxyethoxyethyl methacrylate | 48.0 |
| Ethoxyethoxyethyl methacrylate | 18.0 |
| Diethylene glycol dimethacrylate | 34.4 |
| MEHQ | [100 ppm] |
| BHT | [900 ppm] |
| Dimethyl-p-toluidine | 1.5 |
| | 100.0 percent |
| Poly(ethyl methacrylate) | 98.5 |
| Benzoyl peroxide | 1.5 |
| | 100.0 percent |

The above formulation, when combined, polymerizes to a highly flexible artifical fingernail material.

I claim:

1. A substantially odorless method of making a fingernail prosthesis comprising:
   i) mixing together:
      (a) an odorless, non-toxic liquid binder comprising at least one methacrylate monomer having the following formula:

$$R-O-CH_2CH_2-O-CH_2CH_2-O-CO-C(CH_3)=CH_2$$

where R is $CH_3(CH_2)_n$ and $n = 0-3$
      together with one or more di- or tri- methacrylates, and a tertiary-amine accelerator; and
      (b) a polymeric powder containing a finely divided methacrylate polymer or copolymer, and a peroxide polymerization initiator;
   ii) applying said mixed composition in a dough-like mass to a fingernail form to shape a fingernail thereon; and
   iii) allowing said applied mixed composition to cure and harden in situ for 90 to 180 seconds at ambient temperatures.

2. The method of claim 1 wherein said liquid binder portion is comprised of the following, based upon the total weight of liquid binder:
   (a) from about 10 percent to about 95 percent of a methacrylate monomer of the formula:

$$R-O-CH_2CH_2-O-CH_2CH_2-O-CO-C(CH_3)=CH_2$$

where R is $CH_3(CH_2)_n$ and $n = 0-3$
   (b) from about 4.9 percent to about 89.9 percent of a di- or tri-methacrylate crosslinker, and (c) from about 0.1 percent to about 5.0 percent of a tertiary-amine free-radical polymerization accelerator.

3. The method of claim 2 wherein said liquid binder further comprises a secondary methacrylate monomer comprising hydroxyethy methacrylate.

4. The method of claim 1 wherein said liquid binder further comprises a polymerization inhibitor selected from butylated hydroxytoluene and the methyl ether of hydroquinone (MEHQ).

5. The method of claim 1 wherein said liquid binder further comprises light stabilizers comprising 2-hydroxy-4-methoxy-benzophenone.

6. The method of claim 1 wherein said liquid binder further comprises dye.

7. The method of claim 1 wherein said methacrylate monomers are selected from methoxyethoxyethyl methacrylate and ethoxyethoxyethyl methacrylate.

8. The method of claim 1 wherein said tertiary amine accelerators are selected from N,N-dimethyl-p-toluidine, N,N-dihydroxyethyl-p-toluidine, N,N-dimethyl aniline, and 4-(dimethylamino)phenethyl alcohol 9. The method of claim 8 wherein said tertiary amine accelerator is in a concentration of from about 0.1 percent to about 5.0 percent by weight of liquid binder.

10. The method of claim 8 wherein said tertiary amine accelerators are selected from N,N-dimethyl-p-toluidine and N,N-dihydroxyethyl-p-toluidine.

11. The method of claim 1 wherein said methacrylate cross-linkers are selected from ethylene glycol dimethacrylate, diethylene glycol dimethacrylate, triethylene glycol dimethacrylate, tetraethylene glycol dimethacrylate, polyethylene glycol dimethacrylate, dipropylene glycol dimethacrylate, tripropylene glycol dimethacrylate, 1,4-butanediol dimethacrylate, 1,3-butanediol dimethacrylate, 1,6-hexanediol dimethacrylate, 1,5-hexanediol dimethacrylate, neopentyl glycol dimethacrylate, 1,12-dodecanediol dimethacrylate, 2,2-bis[4'-(3''-methacryloyl-2''-hydroxypropoxy)phenyl]propane (bis-GMA), 2,2-bis(4'-methacryloyl phenyl)propane (bis-phenol A dimethacrylate), ethoxylated bisphenol A dimethacrylate, tetraethoxylated bis-phenol A dimethacrylate, dimethacrylate-terminated aliphatic and aromatic urethanes, trimethylolpropane trimethacrylate, pentaerythritol tetramethacrylate, and mixtures thereof hydroxyethyl methacrylate adducts of styrene/maleic anhydride copolymers and methyl vinyl ether/maleic anhydride copolymers.

12. The method of claim 1 wherein the polymeric powder portion is comprised of the following ingredients, based upon the dry weight of polymeric powder:
   (a) from about 95 percent to about 99.5 percent of a finely divided polymer selected from poly(ethyl methacrylate), poly(ethyl-co-butyl methacrylate), poly(ethyl-co-methyl methacrylate), poly(methyl-co-butyl methacrylate) and mixtures thereof; and
   (b) from about 0.5 percent to about 3.0 percent of a peroxide free-radical polymerization initiator.

13. The method of claim 1 wherein the polymeric powder portion further comprises additives selected from pigments comprising titanium dioxide, secondary polymers comprising finely divided poly(vinyl acetate) and flow modifiers comprising fumed silica.

14. The method of claim 12 wherein said finely divided polymers or copolymers are in a concentration of from about 80 percent to about 99.5 percent by weight of polymeric powder.

15. The method of claim 1 wherein the ratio of liquid portion to powder portion is from about 1 to 3 to about 2 to 1 by weight.

* * * * *

UNITED STATES PATENT AND TRADEMARK OFFICE
CERTIFICATE OF CORRECTION

PATENT NO.  : 5,098,696
DATED       : March 24-1992
INVENTOR(S) : Montgomery

It is certified that error appears in the above-identified patent and that said Letters Patent is hereby corrected as shown below:

at column 2, line 51:  -- preclude -- for "prelude"

at column 3, line 52,  -- tertiary amine -- for "tertiaryamine"

at column 7, line 23:  -- available -- for "avialable"

at column 8, line 34:  -- artificial -- for "artifical"

at column 10, line 5,  -- bis-phenol -- for "bisphenol"

Signed and Sealed this

Twenty-eight Day of March, 1995

Attest:

BRUCE LEHMAN

*Attesting Officer*     *Commissioner of Patents and Trademarks*